US011919429B2

(12) United States Patent
Goemer et al.

(10) Patent No.: US 11,919,429 B2
(45) Date of Patent: Mar. 5, 2024

(54) ROTATABLE SURFACE APPARATUSES FOR SANITIZING AN UNUSED SURFACE OF A VEHICLE

(71) Applicant: Toyota Motor North America, Inc., Plano, TX (US)

(72) Inventors: David M. Goemer, Frisco, TX (US); Evan Vijithakumara, Frisco, TX (US); Imad Zahid, Carrollton, TX (US); Lou Pope, Flower Mound, TX (US); Yuho Kozu, Dallas, TX (US); Lizbeth Jurado, El Paso, TX (US)

(73) Assignee: Toyota Motor North America, Inc., Plano, TX (US)

( * ) Notice: Subject to any disclaimer, the term of this patent is extended or adjusted under 35 U.S.C. 154(b) by 395 days.

(21) Appl. No.: 17/233,725

(22) Filed: Apr. 19, 2021

(65) Prior Publication Data
US 2022/0332230 A1 Oct. 20, 2022

(51) Int. Cl.
| | | |
|---|---|---|
| *A47C 31/11* | (2006.01) | |
| *A47C 31/10* | (2006.01) | |
| *A61L 2/10* | (2006.01) | |
| *A61L 2/20* | (2006.01) | |
| *A61L 2/22* | (2006.01) | |
| *B60N 2/58* | (2006.01) | |
| *B60N 2/60* | (2006.01) | |

(52) U.S. Cl.
CPC ............ *B60N 2/58* (2013.01); *A61L 2/10* (2013.01); *A61L 2/202* (2013.01); *A61L 2/22* (2013.01); *A61L 2202/11* (2013.01); *A61L 2202/14* (2013.01); *A61L 2202/17* (2013.01)

(58) Field of Classification Search
CPC .............. A47K 13/302; A47K 17/003; B60H 1/00742; B60H 3/0035; B60N 2/58
See application file for complete search history.

(56) References Cited

U.S. PATENT DOCUMENTS

| | | |
|---|---|---|
| 5,403,066 A | 4/1995 | Drum |
| 6,655,736 B1 | 12/2003 | Arenas |
| 10,369,239 B2 * | 8/2019 | Dobrinsky ........... A47K 17/003 |
| 2013/0093225 A1 | 4/2013 | Janowski |
| 2015/0291071 A1 | 10/2015 | Thompson |
| 2018/0021465 A1 * | 1/2018 | Dobrinsky ................ E03D 9/08 4/233 |
| 2019/0176768 A1 | 6/2019 | Diaz Garcia et al. |

(Continued)

FOREIGN PATENT DOCUMENTS

| | | |
|---|---|---|
| CN | 2761451 Y | 3/2006 |
| CN | 202896237 U | 4/2013 |
| CN | 109263439 A | 1/2019 |

(Continued)

*Primary Examiner* — Shin H Kim
(74) *Attorney, Agent, or Firm* — Dinsmore & Shohl LLP

(57) ABSTRACT

A rotatable surface apparatus for a vehicle includes a frame including a contact surface, a cover having at least a first surface portion and a second surface portion, a rotating mechanism rotating the cover to selectively position not more than one of the first surface portion and the second surface portion over the contact surface of the frame simultaneously, and a sanitizing mechanism sanitizing the first surface portion and the second surface portion of the cover when positioned within a predetermined proximity of the sanitizing mechanism.

20 Claims, 3 Drawing Sheets

(56) References Cited

U.S. PATENT DOCUMENTS

2020/0198445 A1  6/2020  Line et al.

FOREIGN PATENT DOCUMENTS

| | | |
|---|---|---|
| CN | 208591353 U | 3/2019 |
| CN | 109908388 A | 6/2019 |
| CN | 110065475 A | 7/2019 |
| CN | 209063855 U | 7/2019 |
| CN | 09454607 U | 10/2019 |
| CN | 210970768 U | 7/2020 |
| EP | 3402686 A1 | 11/2018 |
| ES | 1030192 U | 7/1995 |
| JP | 2006341759 A | 12/2006 |
| WO | 2019139743 A1 | 7/2019 |

\* cited by examiner

ROTATABLE SURFACE APPARATUSES FOR SANITIZING AN UNUSED SURFACE OF A VEHICLE

TECHNICAL FIELD

The present specification generally relates to systems and methods for sanitizing interior surfaces of a vehicle and, more specifically, systems and methods for sanitizing one or more surfaces of a vehicle while unused by an occupant.

BACKGROUND

Vehicle surfaces can become contaminated after prolonged use and contact by occupants. This is particularly common in vehicles in which different occupants are regularly entering and exiting the vehicle such as, for example, in ridesharing vehicles. These surfaces, such as vehicle seats and other surfaces regularly contacted by these occupants, may be sanitized, for example, by manually applying a sanitizing agent on the surface and disinfecting the surface. However, this requires a great deal of time and energy and interrupts the normal use of the vehicle in transporting an occupant that is unable to occupy the space being sanitized.

Accordingly, a need exists for improved systems and methods of sanitizing a surface of a vehicle which does not interrupt the normal use of the vehicle and allows occupants to occupy the space or surface being cleaned.

SUMMARY

In one embodiment, a rotatable surface apparatus for a vehicle includes a frame including a contact surface, a cover having at least a first surface portion and a second surface portion, a rotating mechanism rotating the cover to selectively position not more than one of the first surface portion and the second surface portion over the contact surface of the frame simultaneously, and a sanitizing mechanism sanitizing the first surface portion and the second surface portion of the cover when positioned within a predetermined proximity of the sanitizing mechanism.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
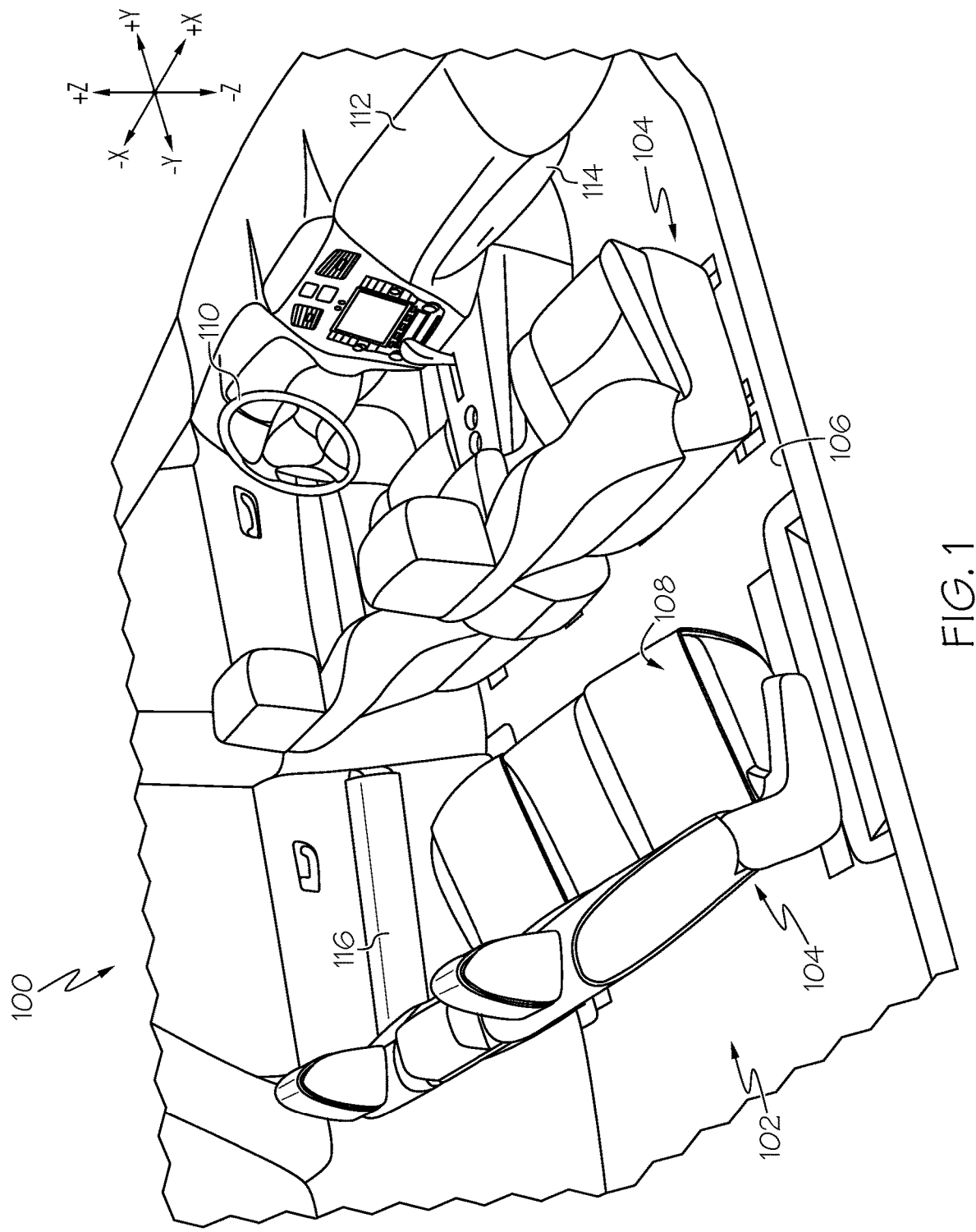
FIG. 1 schematically depicts a perspective view of a passenger compartment of a vehicle including a plurality of vehicle seats, according to one or more embodiments shown and described herein.

Embodiments described herein are directed to a rotatable surface apparatus for a vehicle that includes a rotatable cover that permits one surface portion of the cover to be utilized while at least one other unused surface portion of the cover is being sanitized.

The rotatable surface apparatus includes a frame including a contact surface, a cover having at least a first surface portion and a second surface portion, a rotating mechanism rotating the cover to selectively position not more than one of the first surface portion and the second surface portion over the contact surface of the frame simultaneously, and a sanitizing mechanism sanitizing the first surface portion and the second surface portion of the cover when positioned within a predetermined proximity of the sanitizing mechanism. Various embodiments of the rotatable surface apparatus and the operation of rotatable surface apparatus are described in more detail herein. Whenever possible, the same reference numerals will be used throughout the drawings to refer to the same or like parts.

As used herein, the term "vehicle longitudinal direction" refers to the forward-rearward direction of the vehicle (i.e., in the +/−Y direction of the coordinate axes depicted in FIG. 1). The term "vehicle lateral direction" refers to the cross-vehicle direction (i.e., in the +/−X direction of the coordinate axes depicted in FIG. 1), and is transverse to the vehicle longitudinal direction. The term "vehicle vertical direction" refers to the upward-downward direction of the vehicle (i.e., in the +/−Z direction of the coordinate axes depicted in FIG. 1). As used herein, "upper" and "above" are defined as the positive Z direction of the coordinate axes shown in the drawings. "Lower" and "below" are defined as the negative Z direction of the coordinate axes shown in the drawings.

Referring to FIG. 1, a vehicle 100 is generally illustrated. The vehicle 100 includes a passenger compartment 102 which passengers or other occupants occupy. As shown, a plurality of vehicle seats 104 are provided within the passenger compartment 102 of the vehicle 100. The vehicle seats 104 are mounted above a floor surface 106 of the vehicle 100.

As described in more detail herein, embodiments of rotatable surface apparatuses are provided for sanitizing a surface of the vehicle seat 104 between occupant uses. In embodiments, each vehicle seat 104 may include a rotatable surface apparatus or a plurality of rotatable surface apparatuses 108 for sanitizing a plurality of surfaces of the vehicle seat 104. However, it should be appreciated that the present disclosure is not limited to being utilized on the vehicle seat 104 and is equally applicable to other surfaces of the vehicle 100 that are regularly contacted by an occupant such as, for example, a steering wheel 110, an instrument panel 112, a glove compartment 114, an armrest 116, and the like. In addition, it should be appreciated that although the vehicle 100 depicted herein is illustrated as an automobile, the vehicle 100 may be any other passenger or non-passenger vehicle such as, for example, a terrestrial, aquatic, and/or airborne vehicle.

Figure 2:
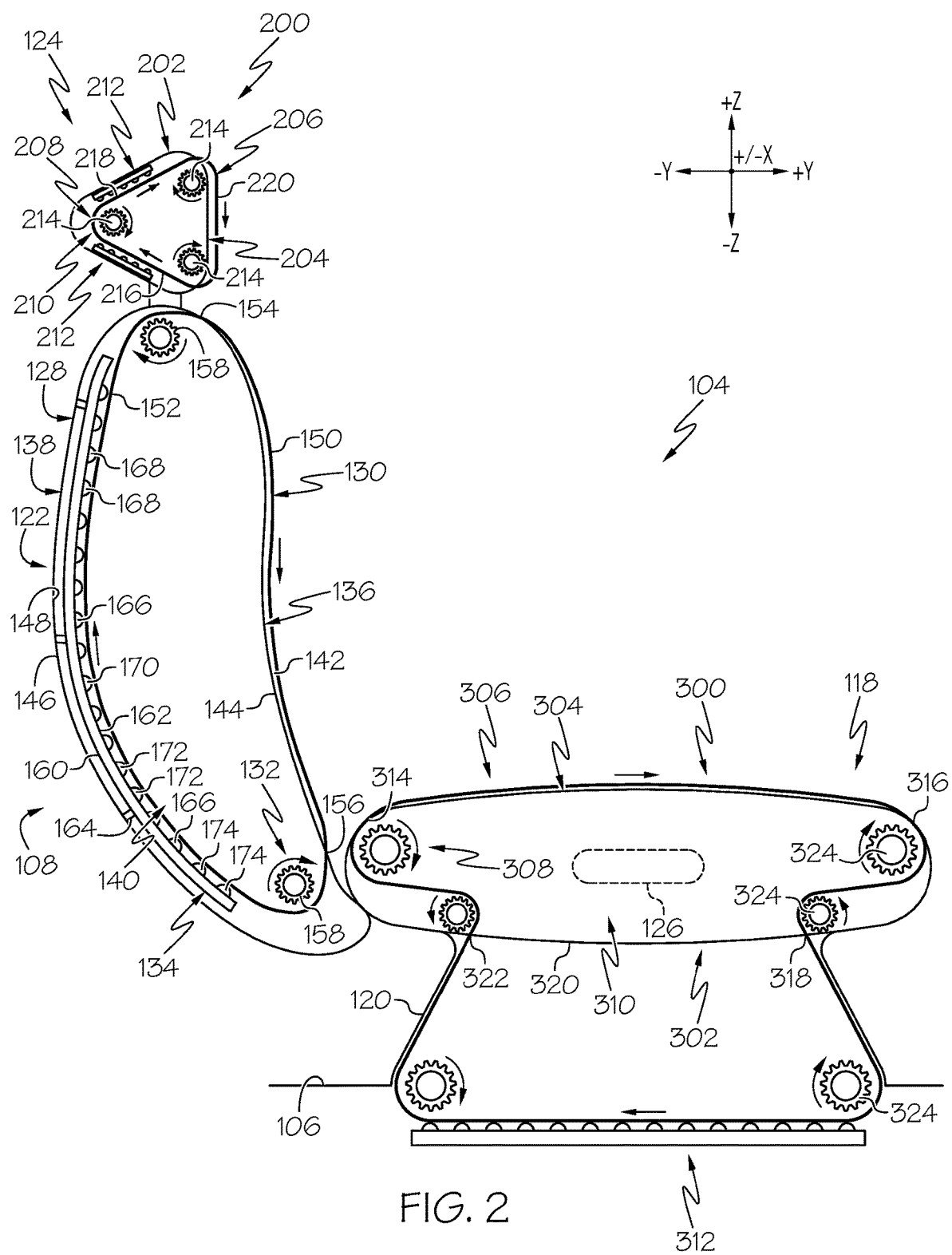
FIG. 2 schematically depicts a cross-sectional side view of a vehicle seat of the vehicle, according to one or more embodiments shown and described herein.

Referring now to FIG. 2, an embodiment of the vehicle seat 104 is illustrated. The vehicle seat 104 includes a seat cushion 118 mounted above the floor surface 106 of the vehicle 100 by a base 120, a seat back 122 pivotally attached to the seat cushion 118, and a headrest 124 mounted to an end of the seat back 122 opposite the seat cushion 118. As described in more detail herein, the vehicle seat 104 includes a plurality of rotatable surface apparatuses 108 for rotating any combination of surfaces on the vehicle seat 104 such as a surface of the seat back 122, the seat cushion 118, and the headrest 124. Thus, each of the seat cushion 118, the seat back 122, and the headrest 124 may include one or more rotatable surface apparatuses 108. In some embodiments, a pressure sensor 126 (or other passenger detection device, such as a heat sensor, image capture device, etc.) may be provided, such as within the seat cushion 118. The pressure sensor 126 is configured to detect a presence of an occupant seated on the vehicle seat 104, specifically the seat cushion 118. As discussed herein, the detection of an occupant being present or getting up from the vehicle seat 104 may instruct the rotatable surface apparatus 108 to activate.

The seat back 122 is illustrated in FIG. 2 as including the rotatable surface apparatus 108. The rotatable surface apparatus 108 includes a seat back frame 128, a cover 130, a rotating mechanism 132 for rotating the cover 130, and a sanitizing mechanism 134 for sanitizing one or more portions of the cover 130. With more particularity, the seat back frame 128 has a contact surface 136 and an opposite distal surface 138 at least partially defining an interior 140 of the seat back frame 128 in which the rotating mechanism 132 is housed and through which the cover 130 extends. The contact surface 136 of the seat back frame 128 has an exterior side 142 and an opposite interior side 144 such that the interior side 144 of the contact surface 136 faces the interior 140 of the seat back frame 128 and the exterior side 142 faces a direction opposite the interior 140. Similarly, the distal surface 138 has an exterior side 146 and an opposite interior side 148 such that the interior side 148 of the distal surface 138 faces the interior 140 of the seat back frame 128 and the exterior side 146 faces a direction opposite the interior 140.

The cover 130 may be formed from any suitable material such as, for example, leather, suede, vinyl, polyester, nylon, and the like. Accordingly, the material comprising the cover 130 is flexible so that the cover 130 may be rolled or otherwise translated across the contact surface 136 of the seat back frame 128. The cover 130 defines at least a first surface portion 150 and a second surface portion 152 extending from the first surface portion 150. The first surface portion 150 and the second surface portion 152 define a circumferential length of the cover 130. As shown, in a first position, the cover 130 extends through the contact surface 136 of the seat back frame 128 such that the first surface portion 150 extends along or adjacent to the exterior side 142 of the contact surface 136 of the seat back frame 128 while the second surface portion 152 of the cover 130 is provided within the interior 140 and extends along or adjacent to the interior side 148 of the distal surface 138 of the seat back frame 128. In embodiments, the cover 130 may exit the interior 140 through a first opening 154 formed in the seat back frame 128 proximate the headrest 124 and return into the interior 140 through a second opening 156 formed in the seat back frame 128 proximate the seat cushion 118.

The rotating mechanism 132 of the rotatable surface apparatus 108 may be at least partially provided within the interior 140 of the seat back frame 128. As shown, the rotating mechanism 132 includes a pair of rollers 158, such as pinions, that are rotatably mounted within the interior 140. However, it should be appreciated that the rotating mechanism 132 may include any other suitable rotation device other than the rollers 158 such as, for example, a track, a conveyor belt system, a pull-chain, and the like. In the present embodiment, the rotating mechanism 132 may include a motor, not shown, for operating the pair of rollers 158 in response to a command or signal received to operate the rotatable surface apparatus 108, as discussed in more detail herein. Each of the rollers 158 contact and engage the cover 130 such that rotation of the rollers 158 causes the cover 130 to rotate in a corresponding direction.

For example, as shown by the arrows, clockwise rotation of the rollers 158 results in clockwise rotation of the cover 130 relative to the seat back frame 128. Thus, the rotating mechanism 132 may be operated to selectively position the first surface portion 150 over the exterior side 142 of the contact surface 136 of the seat back frame 128 and position the second surface portion 152 within the interior 140 along or adjacent to the interior side 148 of the distal surface 138 of the seat back frame 128, as shown in FIG. 2 when in the first position. Further operation of the rotating mechanism 132 may rotate the cover 130 to a second position such that the second surface portion 152 extends along or adjacent to the exterior side 142 of the contact surface 136 of the seat back frame 128 while the first surface portion 150 of the cover 130 is provided within the interior 140 and extends along or adjacent to the interior side 148 of the distal surface 138 of the seat back frame 128.

In embodiments, the rotating mechanism 132 may determine a total distance of rotation or length of travel of the cover 130 based on operating parameters of the rotating mechanism 132, for example, speed, operating time, and the like. This information may be utilized to identify a position of the first surface portion 150 and the second surface portion 152 of the cover 130 at any given time. This information may be further utilized to determine when to activate and deactivate the rotating mechanism 132 to accurately position the first surface portion 150 and the second surface portion 152 relative to the seat back frame 128.

In embodiments, the sanitizing mechanism 134 of the rotatable surface apparatus 108 is provided within the interior 140 and includes a first side 160 facing the interior side 148 of the distal surface 138 of the seat back frame 128, and an opposite second side 162 facing the interior side 144 of the contact surface 136 of the seat back frame 128. In embodiments, the sanitizing mechanism 134 may be mounted to the interior side 148 of the distal surface 138 of the seat back frame 128 in any suitable manner such as, for example, by directly mounting the first side 160 directly to the distal surface 138 of the seat back frame 128, utilizing brackets 164, or the like. The sanitizing mechanism 134 may include one or more sanitizing devices 166 provided on the second side 162 of the sanitizing mechanism 134 for directing a sanitizing agent toward the cover 130. As shown, the sanitizing mechanism 134 includes a plurality of sanitizing devices 166 provided on the second side 162 thereof. In embodiments, one or more of the sanitizing devices 166 may include an ultraviolet or high temperature heat lamp 168, one or more of the sanitizing devices 166 may include a sanitizing spray nozzle 170 for emitting a solution, one or more of the sanitizing devices 166 may include an ozone emitter 172, and one or more of the sanitizing devices 166 may include a vacuum 174. Accordingly, the sanitizing mechanism 134 may include any combination of sanitizing devices 166 for sanitizing the cover 130 in various manners. As shown, the plurality of sanitizing devices 166 extend along a substantially entire length of the sanitizing mechanism 134 to cover a substantial length of the first surface portion 150 or the second surface portion 152 when positioned adjacent the second side 162 of the sanitizing mechanism 134. Alternatively, a single sanitizing device 166, such as a single ultraviolet or high temperature heat lamp 168, spray nozzle 170, ozone emitter 172, or vacuum 174 may be formed to extend along a substantial portion of the length of the second side 162 of the sanitizing mechanism 134.

As described herein, the rotating mechanism 132 may identify a position of the first surface portion 150 and the second surface portion 152 of the cover 130 based on operation of the rotating mechanism 132. Thus, when the rotating mechanism 132 determines that the first surface portion 150 or the second surface portion 152 is positioned within a predetermined proximity of the sanitizing mechanism 134, the sanitizing mechanism 134 may be activated to emit the sanitizing agent onto the cover 130. As a result, when the cover 130 is rotated to the first position such that the second surface portion 152 is positioned within the interior 140 of the seat back frame 128 and within the predetermined proximity of the sanitizing mechanism 134, such that the first surface portion 150 is positioned along or adjacent to the exterior side 142 of the contact surface 136 of the seat back frame 128, the sanitizing mechanism 134 is activated to emit the sanitizing agent onto the second surface portion 152 of the cover 130. Similarly, when the cover 130 is rotated to the second position such that the first surface portion 150 is positioned within the interior 140 of the seat back frame 128 and within the predetermined proximity of the sanitizing mechanism 134, such that the second surface portion 152 is positioned along or adjacent to the exterior side 142 of the contact surface 136 of the seat back frame 128, the sanitizing mechanism 134 is activated to emit the sanitizing agent onto the first surface portion 150 of the cover 130.

Referring still to FIG. 2, the headrest 124 is illustrated including another embodiment of a rotatable surface apparatus 200. As described in more detail herein, it should be appreciated that the rotatable surface apparatus 200 is substantially similar to the rotatable surface apparatus 108 of the seat back 122. Accordingly, the rotatable surface apparatus 200 includes a headrest frame 202 having a contact surface 204, a cover 206, similar to the cover 130, a rotating mechanism 208, similar to the rotating mechanism 132, for rotating the cover 206 through an interior 210 of the headrest frame 202 and across the contact surface 204 of the headrest frame 202, and a sanitizing mechanism 212, similar to the sanitizing mechanism 134, provided within the interior 210 of the headrest frame 202.

However, as opposed to the rotating mechanism 132 of the rotatable surface apparatus 108 of the seat back 122, which includes a pair of rollers 158 and one sanitizing mechanism 134, the rotatable surface apparatus 200 of the rotating mechanism 208 of the rotatable surface apparatus 200 of the headrest 124 includes three rollers 214 and a pair of sanitizing mechanisms 212. Thus, the rollers 214 shape the cover 206 into a substantially triangular geometry, thereby defining a first surface portion 216, a second surface portion 218, and a third surface portion 220. This allows the first surface portion 216, the second surface portion 218, and the third surface portion 220 to be sequentially positionable across the contact surface 204 of the headrest frame 202, rather than alternatively positioning the first surface portion 150 and the second surface portion 152 of the cover 130 of the rotatable surface apparatus 108 of the seat back 122.

It should be appreciated that by providing three distinct surface portions, i.e., the first surface portion 216, the second surface portion 218, and the third surface portion 220, two of the surface portions 216, 218, 220 of the cover 206 may be simultaneously sanitized by a corresponding sanitizing mechanism 212 while the remaining surface portion 216, 218, 220 extends along the contact surface 204 of the headrest frame 202 to be used by an occupant. For example, as shown, the first surface portion 216 and the second surface portion 218 may be simultaneously sanitized while the third surface portion 220 extends along the contact surface 204 of the headrest frame 202.

Referring still to FIG. 2, the seat cushion 118 is illustrated including another embodiment of a rotatable surface apparatus 300. As described in more detail herein, it should be appreciated that the rotatable surface apparatus 300 is substantially similar to the rotatable surface apparatus 108 of the seat back 122. Accordingly, the rotatable surface apparatus 300 includes a seat cushion frame 302 having a contact surface 304, a cover 306, similar to the cover 130, a rotating mechanism 308, similar to the rotating mechanism 132, for rotating the cover 306 through an interior 310 of the seat cushion frame 302 and across the contact surface 304 of the seat cushion frame 302, and a sanitizing mechanism 312, similar to the sanitizing mechanism 134.

However, unlike the rotatable surface apparatus 108 of the seat back 122 and the rotatable surface apparatus 200 of the headrest 124 in which the sanitizing mechanisms 134, 212 are positioned within the seat back frame 124 and the headrest frame 202, respectively, the sanitizing mechanism 312 of the rotatable surface apparatus 300 of the seat cushion 118 is located below the seat cushion frame 302. More specifically, the sanitizing mechanism 312 is located below the floor surface 106 of the vehicle 100 such that the sanitizing mechanism 312 may be accessed separate from the seat cushion 118 itself. By providing the sanitizing mechanism 312 below or within the floor surface 106 of the vehicle 100, the total length of the cover 306 is increased to allow the cover 306 to extend along the contact surface 304 of the seat cushion frame 302, through the interior 310 of the seat cushion frame 302, and still extend across the sanitizing mechanism 312 below the seat cushion 118. The increased length of the cover 306 also provides additional surface portions of the cover 306 to be independently provided at the contact surface 304 of the seat cushion frame 302.

As the rotating mechanism 308 is operated to rotate the cover 306, the cover 306 may initially exit the interior 310 of the seat cushion frame 302 through a first opening 314 formed in the contact surface 304 of the seat cushion frame 302 proximate the seat back frame 128 and return into the interior 310 through a second opening 316 formed in the contact surface 304 of the seat cushion frame 302 opposite the seat back frame 128. Additionally, the cover 306 may be guided to exit the interior 310 of the seat cushion frame 302 a second time through a third opening 318 formed in a distal surface 320 of the seat cushion frame 302 opposite the seat back frame 128 and return into the interior 310 through a fourth opening 322 formed in the distal surface 320 of the seat cushion frame 302 proximate the seat back frame 128. After exiting the interior 310 through the third opening 318, the cover 306 is guided under the seat cushion 118, through the base 120, and into or through the floor surface 106 of the vehicle 100 in which the sanitizing mechanism 312 is located. To guide the cover 306 along the contact surface 304 of the seat cushion frame 302, through the interior 310, through the floor surface 106 of the vehicle 100, and back into the interior 310, the rotating mechanism 308 may include a plurality of rollers 324, such as the rollers 158, as shown. Alternatively, as discussed herein, the rotating mechanism 308 may include a conveyor belt, track, or the like for guiding the cover 306 in the manner discussed herein.

It should be appreciated that the various embodiments discussed herein are provided for illustrative purposes only and not intended to be limiting to the present disclosure.

Specifically, it is within the scope of the present disclosure that the various embodiments discussed herein may be incorporated into any suitable surface of the vehicle 100 as opposed to the seat cushion 118, the seat back 122, and the headrest 124 detailed herein. As further non-limiting examples, the present disclosure is equally applicable to any suitable surface of the vehicle 100 such as those illustrated in FIG. 1, for example, the steering wheel 110, the instrument panel 112, the glove compartment 114, the armrest 116, and the like. Furthermore, the features of the embodiments of the rotatable surface apparatuses 108, 200, 300 discussed herein are not exclusive of one another and may be combined in any suitable arrangement. For example, the rotatable surface apparatuses 108, 300 of the seat back 122 and the seat cushion 118, respectively, may include a plurality of sanitizing mechanisms 134, 212 for simultaneously sanitizing a plurality of surface portions of a cover, such as with the rotatable surface apparatus 200 of the headrest 124. Similarly, the sanitizing mechanisms 132, 212 of the seat back 122 and the headrest 124, respectively, may be provided outside of the seat back 122 and the headrest 124 themselves, such as with the rotatable surface apparatus 300 of the seat cushion 118.

Figure 3:
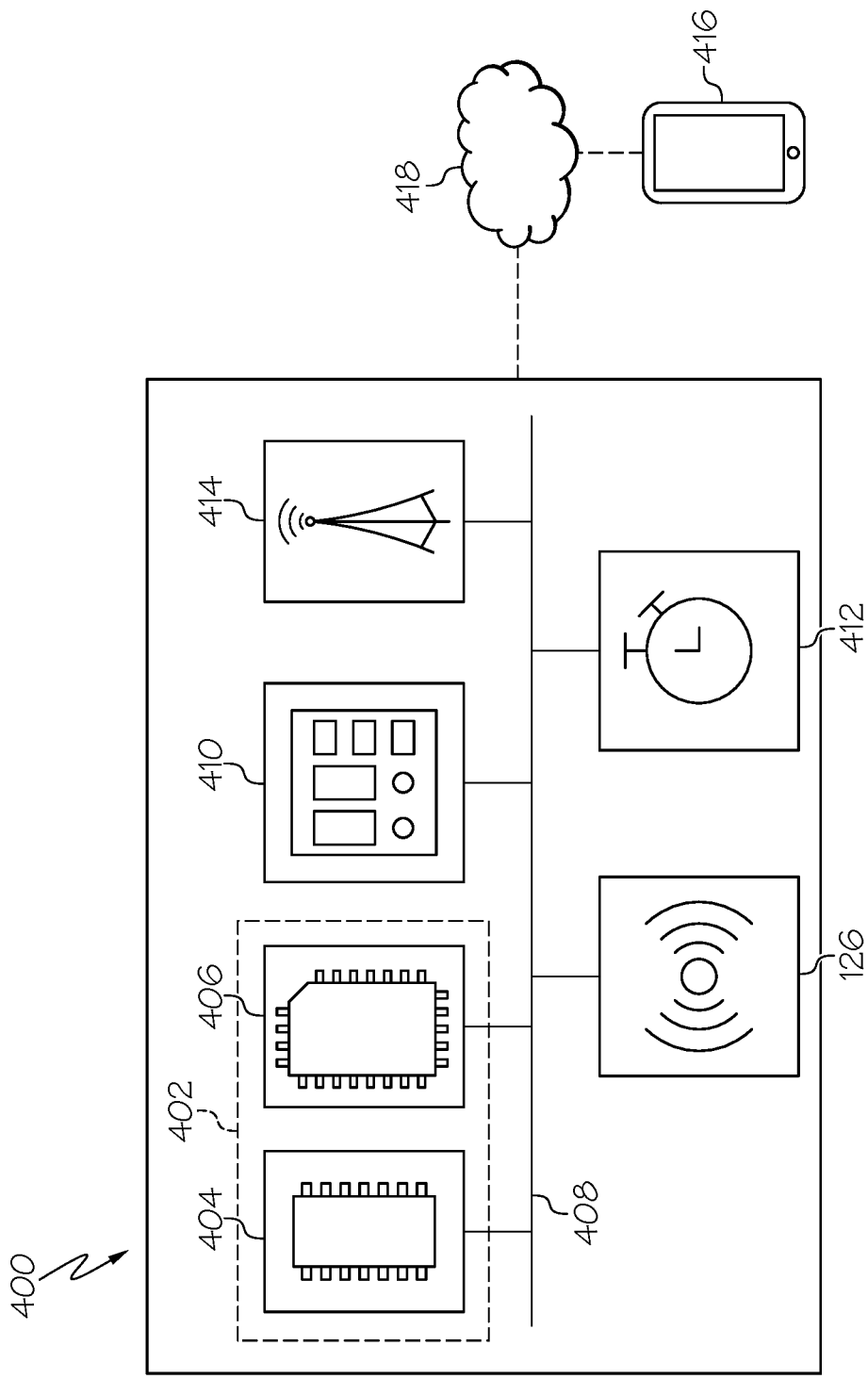
FIG. 3 schematically depicts a control system for operating a rotatable surface apparatus of the vehicle seat of FIG. 2, according to one or more embodiments shown and described herein.

Referring now to FIG. 3, and with reference to the vehicle 100 illustrated in FIGS. 1 and 2, a schematic diagram of a control system 400 for operating one or more of the rotatable surface apparatuses 108, 200, 300 discussed herein is depicted. While the control system 400 is depicted in isolation, the control system 400 may be included within the vehicle 100 of FIG. 1. Without limiting the present disclosure, reference to the operation of the control system 400 may be made to the control system 400 operating the rotatable surface apparatus 108 of the seat back 122. However, operation of the control system 400 is equally applicable to the other embodiments discussed herein.

The control system 400 includes a controller 402 including one or more processors 404 and one or more memory modules 406. Each of the one or more processors 404 may be any device capable of executing machine readable and executable instructions. Accordingly, each of the one or more processors 404 may be an integrated circuit, a microchip, a computer, or any other computing device. The one or more processors 404 are coupled to a communication path 408 that provides signal interconnectivity between various modules of the control system 400. Accordingly, the communication path 408 may communicatively couple any number of processors 404 with one another, and allow the modules coupled to the communication path 408 to operate in a distributed computing environment. Specifically, each of the modules may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 408 may be formed from any medium that is capable of transmitting a signal such as, for example, conductive wires, conductive traces, optical waveguides, or the like. In some embodiments, the communication path 408 may facilitate the transmission of wireless signals, such as WiFi, Bluetooth®, Near Field Communication (NFC) and the like. Moreover, the communication path 408 may be formed from a combination of mediums capable of transmitting signals. In one embodiment, the communication path 408 comprises a combination of conductive traces, conductive wires, connectors, and buses that cooperate to permit the transmission of electrical data signals to components such as processors, memories, sensors, input devices, output devices, and communication devices. Accordingly, the communication path 408 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

As noted above, the control system 400 includes one or more memory modules 406 coupled to the communication path 408. The one or more memory modules 406 may comprise RAM, ROM, flash memories, hard drives, or any device capable of storing machine readable and executable instructions such that the machine readable and executable instructions can be accessed by the one or more processors 404. The machine readable and executable instructions may comprise logic or algorithm(s) written in any programming language of any generation (e.g., 1GL, 2GL, 3GL, 4GL, or 5GL) such as, for example, machine language that may be directly executed by the processor, or assembly language, object-oriented programming (OOP), scripting languages, microcode, etc., that may be compiled or assembled into machine readable and executable instructions and stored on the one or more memory modules 406. Alternatively, the machine readable and executable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components.

The control system 400 also includes the user control device 410 coupled to the communication path 408. The user control device 410 includes one or more controls for manually operating the rotatable surface apparatuses 108, 200, 300. More particularly, with respect to the rotatable surface apparatus 108 of the seat back 122, the controls of the user control device 410 may be utilized to initiate rotation of the cover 130 via the rotating mechanism 132 and, in response, actuation of the sanitizing mechanism 134. The one or more controls of the user control device 410 may include, for example, buttons or the like. In some embodiments, the user control device 410 includes a user interface, such as a touch screen user interface. As such, the user control device 410 may be included or incorporated into a display device.

In embodiments, the control system 400 includes the pressure sensor 126 within the seat cushion 118, discussed herein, which is coupled to the communication path 408 for monitoring the presence of an occupant in the vehicle seat 104. For example, in response to the pressure sensor 126 determining that an occupant is no longer seated in the vehicle seat 104, the rotatable surface apparatus 108 of the seat back 122, for example, may be operated to automatically rotate the cover 130 and actuate the sanitizing mechanism 134.

In embodiments, the control system 400 includes a timer 412 coupled to the communication path 408. The timer 412 may be utilized for automatically operating the rotatable surface apparatuses 108, 200, 300 after a predetermined period of time. For example, in response to determining that no occupant is present within the vehicle seat 104 and a predetermined period of time has elapsed, the rotatable surface apparatus 108 of the seat back 122, for example, may be operated to automatically rotate the cover 130 such that one of the first surface portion 150 and the second surface portion 152 is positioned along the contact surface 136 of the seat back frame 128, and actuate the sanitizing mechanism 134 to sanitize the other of the of the first surface portion 150 and the second surface portion 152 when positioned within the predetermined distance of the sanitizing mechanism 134.

In embodiments, the control system 400 includes network interface hardware 414 for communicatively coupling the control system 400 to a remote device 416 such as, for example, a mobile device, via a network 418. The network interface hardware 414 can be communicatively coupled to the communication path 408 and can be any device capable of receiving and transmitting data via the network 418. Accordingly, the network interface hardware 414 can include a communication transceiver for sending and/or receiving any wired or wireless communication. For example, the network interface hardware 414 may include an antenna, a modem, LAN port, Wi-Fi card, WiMax card, mobile communications hardware, near-field communication hardware, satellite communication hardware and/or any wired or wireless hardware for communicating with other networks and/or devices. In one embodiment, the network interface hardware 414 includes hardware configured to operate in accordance with the Bluetooth® wireless communication protocol. For example, the network interface hardware 414 of the control system 400 may receive an instruction from the remote device 416 and, subsequently, transmit the instruction to the rotatable surface apparatuses 108, 200, 300 to operate in response to receiving the instruction.

From the above, it is to be appreciated that defined herein is a rotatable surface apparatus for a vehicle that rotates a cover extending over a contact surface away from the contact surface. Accordingly, a contaminated or previously used surface portion of the cover is rotated away so that the previously used surface can be sanitized by a sanitizing mechanism. Simultaneously, the cover is rotated so that an uncontaminated surface portion of the cover, which has have been recently sanitized, is provided to extend over the contact surface to be used by the occupant while the previously used surface portion is being sanitized.

While particular embodiments have been illustrated and described herein, it should be understood that various other changes and modifications may be made without departing from the scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A rotatable surface apparatus for a vehicle comprising:
   a frame including a contact surface and a distal surface opposite the contact surface, the contact surface configured to face an occupant;
   a cover having at least a first surface portion and a second surface portion;
   a rotating mechanism rotating the cover to selectively position not more than one of the first surface portion and the second surface portion over the contact surface of the frame simultaneously; and
   a sanitizing mechanism sanitizing the first surface portion and the second surface portion of the cover when positioned within a predetermined proximity of the sanitizing mechanism, the first surface portion and the second surface portion of the cover determined to be within the predetermined proximity when over the distal surface of the frame and not be within the predetermined proximity when over the contact surface of the frame.

2. The rotatable surface apparatus of claim 1, wherein:
   the cover includes a third surface portion;
   the rotating mechanism is configured to rotate the cover to selectively position not more than one of the first surface portion, the second surface portion, and the third surface portion over the contact surface of the frame simultaneously;
   the sanitizing mechanism includes a first sanitizing mechanism and a second sanitizing mechanism; and
   when the third surface portion is positioned over the contact surface of the frame, the first surface portion is positioned to be sanitized by the first sanitizing mechanism and the second surface portion is positioned to be sanitized by the second sanitizing mechanism.

3. The rotatable surface apparatus of claim 1, wherein the sanitizing mechanism is positioned within the frame.

4. The rotatable surface apparatus of claim 3, wherein the rotating mechanism guides the cover into an interior of the frame through a first opening formed in the contact surface and proximate a first end of the frame, and out of the interior of the frame through a second opening formed in the contact surface and proximate an opposite second end of the frame.

5. The rotatable surface apparatus of claim 1, wherein the sanitizing mechanism is positioned outside of the frame.

6. The rotatable surface apparatus of claim 1, wherein the sanitizing mechanism comprises one or more of an ultraviolet or heat lamp, a spray nozzle, an ozone emitter, and a vacuum.

7. The rotatable surface apparatus of claim 6, wherein the sanitizing mechanism comprises a plurality of spray nozzles extending along a length of the sanitizing mechanism.

8. The rotatable surface apparatus of claim 1, wherein the rotating mechanism comprises a plurality of rollers positioned at opposite ends of the frame to guide the cover through the frame.

9. The rotatable surface apparatus of claim 1, wherein the frame comprises one of a seat back frame, a seat cushion frame, and a headrest frame.

10. The rotatable surface apparatus of claim 9, further comprising:
    a pressure sensor provided within the seat cushion frame; and
    a controller configured to operate the rotating mechanism and the sanitizing mechanism in response to the pressure sensor detecting that an occupant is no longer present on the seat cushion frame.

11. A rotatable surface apparatus for a vehicle comprising:
    a frame including a contact surface;
    a cover having at least a first surface portion and a second surface portion;
    a rotating mechanism rotating the cover to selectively position not more than one of the first surface portion and the second surface portion over the contact surface of the frame simultaneously; and
    a sanitizing mechanism sanitizing the first surface portion and the second surface portion of the cover when positioned within a predetermined proximity of the sanitizing mechanism,
    wherein the sanitizing mechanism is positioned within the frame.

12. The rotatable surface apparatus of claim 11, wherein the rotating mechanism guides the cover into an interior of the frame through a first opening formed in the contact surface and proximate a first end of the frame, and out of the interior of the frame through a second opening formed in the contact surface and proximate an opposite second end of the frame.

13. The rotatable surface apparatus of claim 11, wherein the sanitizing mechanism comprises one or more of an ultraviolet or heat lamp, a spray nozzle, an ozone emitter, and a vacuum.

14. The rotatable surface apparatus of claim 13, wherein the sanitizing mechanism comprises a plurality of spray nozzles extending along a length of the sanitizing mechanism.

15. The rotatable surface apparatus of claim 11, wherein the rotating mechanism comprises a plurality of rollers positioned at opposite ends of the frame to guide the cover through the frame.

16. The rotatable surface apparatus of claim 11, wherein the frame comprises one of a seat back frame, a seat cushion frame, and a headrest frame.

17. The rotatable surface apparatus of claim 16, further comprising:
a pressure sensor provided within the seat cushion frame; and
a controller configured to operate the rotating mechanism and the sanitizing mechanism in response to the pressure sensor detecting that an occupant is no longer present on the seat cushion frame.

18. A rotatable surface apparatus for a vehicle comprising:
a frame including a contact surface;
a cover having at least a first surface portion and a second surface portion;
a rotating mechanism rotating the cover to selectively position not more than one of the first surface portion and the second surface portion over the contact surface of the frame simultaneously; and
a sanitizing mechanism sanitizing the first surface portion and the second surface portion of the cover when positioned within a predetermined proximity of the sanitizing mechanism,
wherein the rotating mechanism comprises a plurality of rollers positioned at opposite ends of the frame to guide the cover through the frame.

19. The rotatable surface apparatus of claim 18, wherein the sanitizing mechanism is positioned outside of the frame.

20. The rotatable surface apparatus of claim 18, wherein the sanitizing mechanism comprises one or more of an ultraviolet or heat lamp, a spray nozzle, an ozone emitter, and a vacuum.

* * * * *